US010207049B2

(12) United States Patent
McMichael et al.

(10) Patent No.: US 10,207,049 B2
(45) Date of Patent: Feb. 19, 2019

(54) SINGLE CORE PIN ASSEMBLY THAT CREATES TWO INDEPENDENT VALVE RETAINERS FOR ENTERAL FEEDING HEAD

(71) Applicant: Avent, Inc., Alpharetta, GA (US)

(72) Inventors: Donald McMichael, Roswell, GA (US); Katherine L. Dziak, Alpharetta, GA (US)

(73) Assignee: Avent, Inc., Alpharetta, GA (US)

( * ) Notice: Subject to any disclaimer, the term of this patent is extended or adjusted under 35 U.S.C. 154(b) by 137 days.

(21) Appl. No.: 15/512,959

(22) PCT Filed: Sep. 26, 2014

(86) PCT No.: PCT/US2014/057601
§ 371 (c)(1),
(2) Date: Mar. 21, 2017

(87) PCT Pub. No.: WO2016/048339
PCT Pub. Date: Mar. 31, 2016

(65) Prior Publication Data
US 2017/0296743 A1    Oct. 19, 2017

(51) Int. Cl.
*B29C 45/00* (2006.01)
*A61M 5/168* (2006.01)
(Continued)

(52) U.S. Cl.
CPC ... *A61M 5/16881* (2013.01); *B29C 45/14754* (2013.01); *B29C 45/2628* (2013.01); *B29C 45/44* (2013.01); *B29C 45/4478* (2013.01); *F16K 27/00* (2013.01); *B29C 45/261* (2013.01); *B29C 2045/1477* (2013.01);
(Continued)

(58) Field of Classification Search
CPC .......... A61M 5/16881; A61M 25/0009; B29L 2031/7542; B29C 45/2628; B29C 2045/366
See application file for complete search history.

(56) References Cited

U.S. PATENT DOCUMENTS 3,901,965 A * 8/1975 Honeyman, III . A61M 25/1027
264/275
4,207,900 A * 6/1980 Patel ................. A61M 25/1025
604/103
(Continued)

OTHER PUBLICATIONS

International Search Report for PCT/US2014/057601, dated Dec. 23, 2014, 3 pages.

*Primary Examiner* — Reinaldo Sanchez-Medina
(74) *Attorney, Agent, or Firm* — Dority & Manning, P.A.

(57) ABSTRACT

A single core pin assembly (10) having a first core pin (12) and at least one second core pin (14), the first core pin (12) having a first end (16), a second end (18) and a first core pin body (20). The first core pin body (20) connects the first end (16) and the second end (18). The second core pin (14) has a first end (24), a second end (26), and a second core pin body (28) connecting the second core pin first end (24) and the second core pin second end (26). The second core pin first end (24) is configured to join with the first core pin first end (16) to form a common downstream channel (30). The core pin (10) may be placed in a mold and surrounded by a flowable material (e.g. plastic) to form a work piece.

8 Claims, 8 Drawing Sheets

(51) Int. Cl.
  *B29C 45/26*    (2006.01)
  *B29C 45/44*    (2006.01)
  *B29C 45/14*    (2006.01)
  *F16K 27/00*    (2006.01)
  B29L 31/00      (2006.01)
  B29K 75/00      (2006.01)
  B29K 77/00      (2006.01)
  B29K 101/12     (2006.01)

(52) U.S. Cl.
  CPC ...... *B29K 2075/00* (2013.01); *B29K 2077/00* (2013.01); *B29K 2101/12* (2013.01); *B29L 2031/7506* (2013.01)

(56) References Cited

U.S. PATENT DOCUMENTS

| | | | |
|---|---|---|---|
| 4,284,459 A * | 8/1981 | Patel | A61M 25/1025 156/245 |
| 5,352,215 A | 10/1994 | Thome et al. | |
| 5,798,073 A | 8/1998 | Johnson et al. | |
| 7,708,923 B1 | 5/2010 | Helicke et al. | |
| 7,943,077 B2 * | 5/2011 | Sansoucy | A61M 25/0009 249/64 |
| 2005/0121103 A1 | 6/2005 | Steigerwalt et al. | |
| 2008/0260986 A1 | 10/2008 | Smith | |
| 2014/0004370 A1 | 1/2014 | Kenowski et al. | |

* cited by examiner

US 10,207,049 B2

SINGLE CORE PIN ASSEMBLY THAT CREATES TWO INDEPENDENT VALVE RETAINERS FOR ENTERAL FEEDING HEAD

CROSS-REFERENCE TO RELATED APPLICATIONS

This application is a national phase of and claims priority to PCT/US2014/057601, filed Sep. 26, 2014, the contents of which are incorporated herein by reference.

BACKGROUND OF THE DISCLOSURE

In order to form a hole or channel within a molded part, a core pin is typically used. The pin itself is usually formed of hard steel. During a forming process, after plastic flows around the core pin, the plastic cools and solidifies. When the core pin is pulled out of the part, a void defined by the core pin is formed through the solidified plastic. The void or channel may be a straight channel. Alternatively, the channel may be a non-linear channel as generally described in U.S. Patent Application Publication No. US 2008/0260986 A1 by Smith. Multiple parallel channels may be formed by providing multiple core pins as generally described in U.S. Pat. No. 5,798,073 to Johnson et al. The channels can be used to insert valves into the cooled plastic part and to allow liquid or gas to flow through the channels.

While these references disclose improvements, each fails to recognize or address the need for a molded component that has two independent valves inserted into the cooled plastic part or "head" wherein the channels come together downstream of the valves. Meeting this need is important because molded components having valves with common downstream channels are desirable in applications that involve the monitoring of pressure and transfer or distribution of fluids or liquids. For example, compact components used for the pressure monitoring and transfer of fluids or liquids in various devices including medical devices like enteral feeding devices.

There is a need for molded articles having two (or more) independent valves with common downstream channels that allow for compact construction. The need extends to a system and method for forming molded components having independent valve channels and common downstream channels. There is a need for a system and method for reliable, high-speed and accurate production with low waste.

SUMMARY OF THE DISCLOSURE

The problems described above are addressed by the disclosed single core pin that creates two independent valve channels and a common downstream channel. The single core pin assembly has a first core pin and at least one second core pin. The first core pin has a first end, a second end and a first core pin body. The first core pin body connects the first end and the second end. The second core pin has a first end, a second end, and a second core pin body connecting the second core pin first end and the second core pin second end. The second core pin first end is configured to join with the first core pin first end to form a common downstream channel.

The core pin may be placed in a mold and surrounded by a flowable material (e.g. plastic) to form a work piece. When the core pin is removed from the work piece a molded component is formed. The molded component defines connected voids into which valves may be inserted and which extend into a common downstream channel. The common downstream channel is adapted to be fluidly connected to a catheter lumen. An adhesive is used to secure the valves to the molded component and to seal the space between the valves in the molded component.

Figure 1:
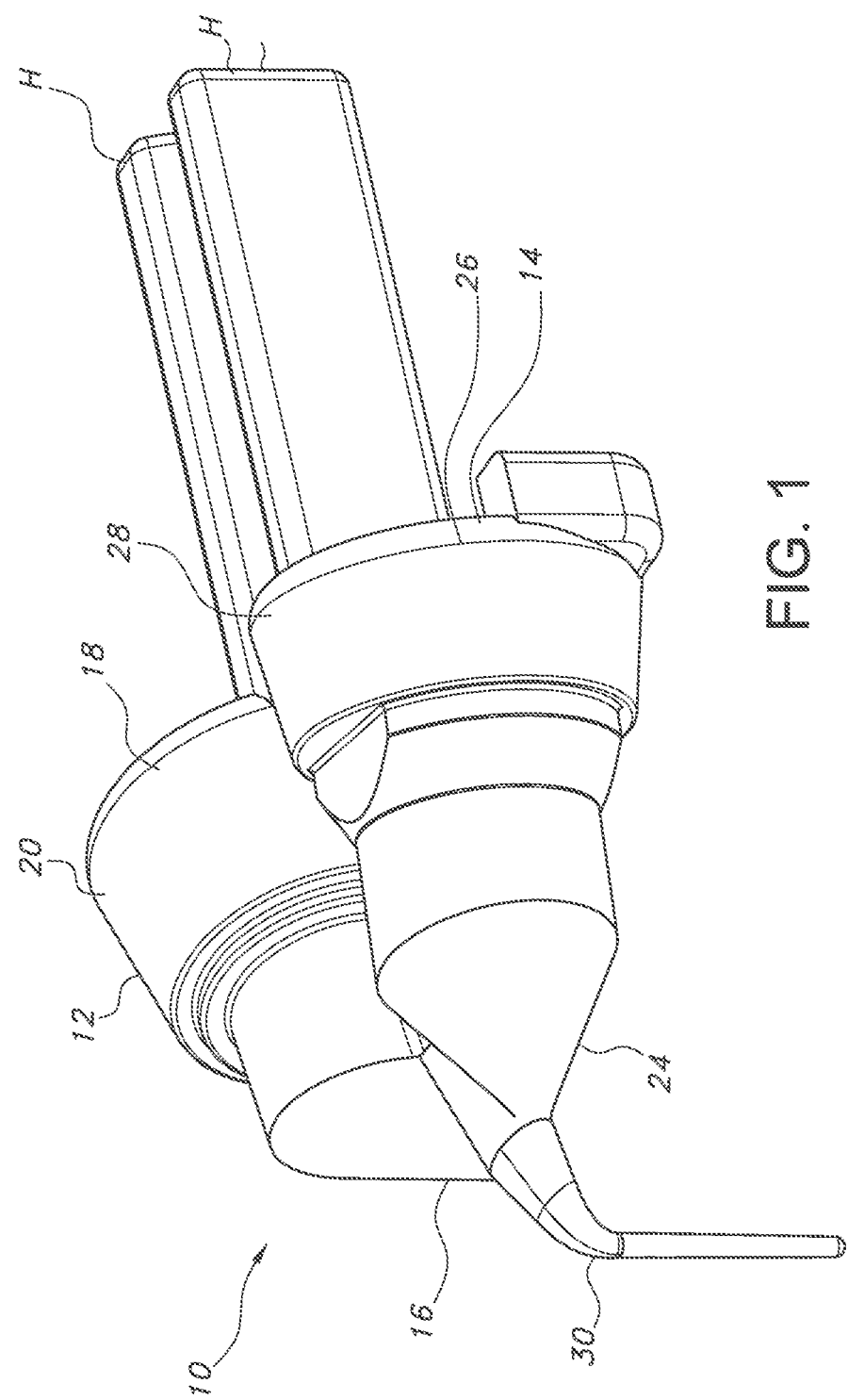
FIG. 1 is a side perspective view illustration of an exemplary single core pin assembly showing an exemplary first core pin and an exemplary second core pin.

Repeat use of reference characters in the present specification and drawings is intended to represent the same or analogous features or elements of the disclosure.

DETAILED DESCRIPTION OF THE DISCLOSURE

Reference will now be made in detail to one or more embodiments, examples of which are illustrated in the drawings, such drawings are not necessarily to scale. It should be understood that features illustrated or described as part of one embodiment may be used with another embodiment to yield still a further embodiment.

Turning now to the drawings, there is shown in side perspective view at FIG. 1, an exemplary single core pin assembly 10 composed of a first core pin 12 and at least one second core pin 14. The first core pin 12 has a first end 16, a second end 18 and a first core pin body 20 connecting the first end 16 and the second end 18. The second core pin 14 has a first end 24, a second end 26, and a second core pin body 28 connecting the first end 24 and the second end 26 of the secondary core pin 14. The second core pin first end 24 is configured to join with the first core pin first end 16 to form a common downstream channel 30.

Figure 2:
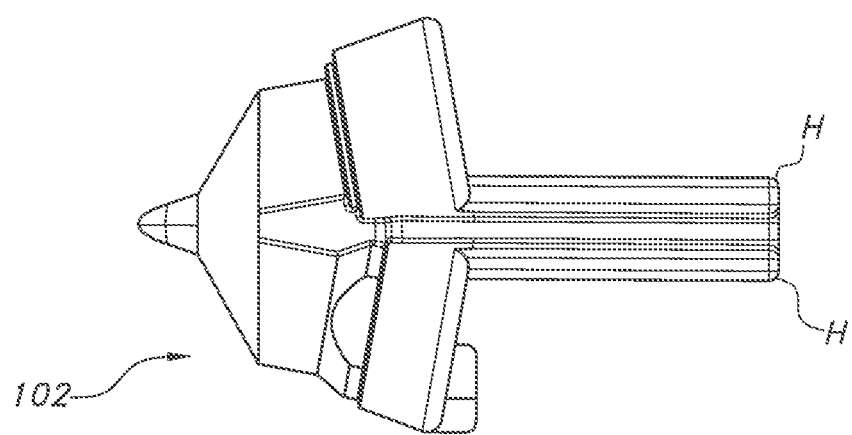
FIG. 2 shows a top view of the single core pin of FIG. 1 where the separate handles are more clearly visible.

A handle or prong "H" extending from each respective core pin body 20, 28 is shown in broken lines only in FIG. 1. Such handle "H" is used to hold and manipulate the core pin and extract the core pin from a molded article or component. FIG. 2 shows a top view of the single core pin 10 of FIG. 1 where the separate handles "H" are more clearly visible.

Desirably, the core pins may be formed of plastic. Even more desirably, the core pins may be formed of a flexible plastic that can flex as it is withdrawn from a molded article formed around the core pin. The plastic should have a higher melting point than the flowable material used with the core pins to form a molded component.

As can be seen in the Figures, the core pins can be funnel-shaped. That is, the core pins may generally taper from a first end to a second opposite end. The taper may be gradual and consistent or it may vary to form, for example, channels having a large diameter at one end that tapers sharply to a first, smaller diameter and then tapers much more gradually to a second, smaller diameter. It is contemplated that the core pins may have a variety of shapes or configurations. For example, the core pin may have a round cross-section, a triangular cross-section, a rectangular cross-section, a square cross-section, a pentagonal (or other polygonal) cross-section, and combinations of the same.

Figure 3:
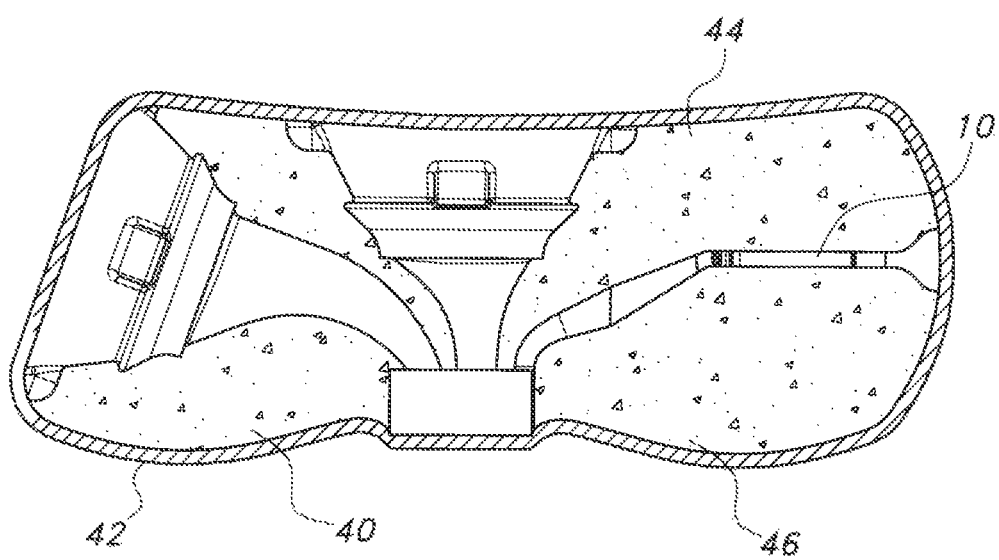
FIG. 3 is a cross sectional view of a flowable material such as, for example, a thermoplastic polymer after it is injected into the molding chamber or forming device via a sprue (not shown) and has flowed around the single core pin assembly to form a work piece composed of a molded component and the single core pin assembly.

According to the system, a flowable material such as, for example, a thermoplastic polymer (i.e. plastic) 40 is injected into the mold, molding chamber or forming device 42 via a sprue (not shown) and flows around the single core pin assembly 10 to form a work piece 44 shown in cross-section in FIG. 3 and composed of a molded component 46 and the single core pin assembly 10. Note that in this and other figures, other voids from other core pins may be seen. These other core pins and voids are to provide other functionality to the molded component but are not the subject of this disclosure. Exemplary polymers used to form the molded component include polyurethanes, polyamides, polyolefins, and polytetrafluoroethlylenes. Depending on the polymer chosen, it may be desirable to allow the core pin to remain in the molded component for an extended length of time since some plastics take longer to set than others.

Figure 4:
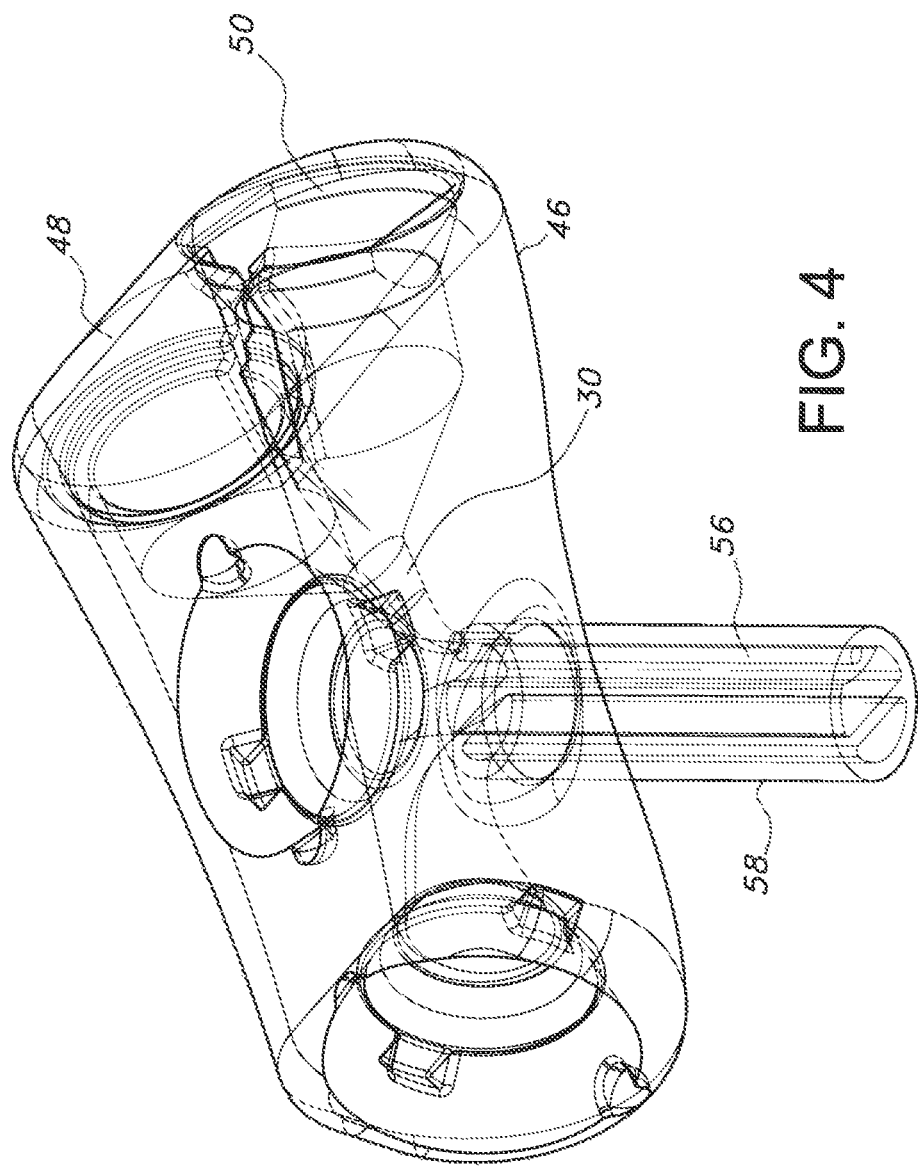
FIG. 4 is a side perspective view illustration of an exemplary molded component formed by the removal of the single core pin assembly from a work piece showing the connected voids and downstream channel.

Referring to FIG. 4, when the single core pin assembly 10 is removed from the molded component 46 after the plastic polymer 40 is solidified (either while the molded component 46 is retained within the forming device 42 or after the molded component 46 is extracted from the forming device 42); the molded component 46 defines connected voids 48, 50.

The present disclosure also encompasses a molded work piece 44. The molded work piece includes: a molded body component 46 formed of a plastic 40 material; and a single core pin assembly 10 positioned within the body. The single core pin assembly is an assembly as described above. Plastic material surrounds the single core pin assembly so the single core pin assembly defines a structure having two core pins with a common downstream channel.

Figure 5:
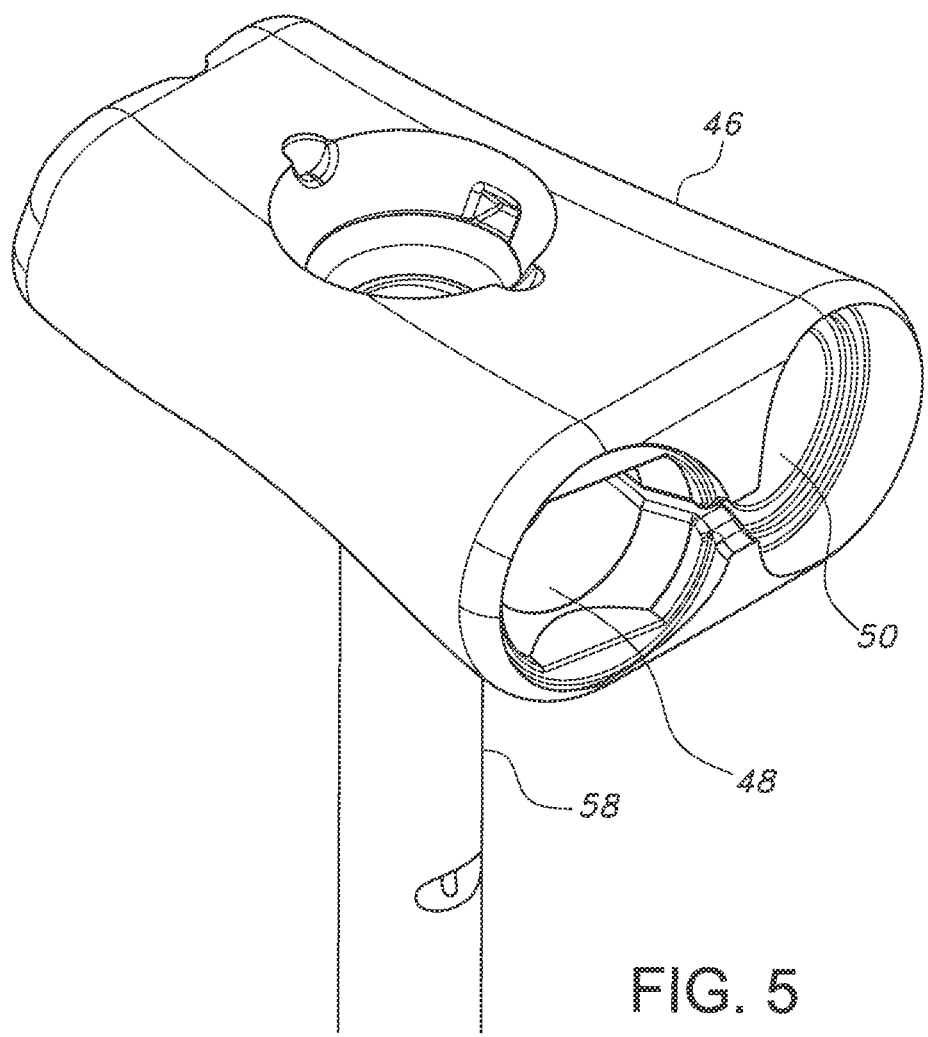
FIG. 5 is an end perspective view illustration of an exemplary molded component formed by the removal of the single core pin assembly from a work piece showing the connected voids and downstream channel.

Upon removal of the single core pin assembly 10 from the molded work piece 44, the molded body component 46 defines connected voids into which valves may be inserted and which extend into a downstream channel 30. FIG. 4 shows a perspective view of the molded component 46 with the connected voids 48, 50 visible. FIG. 5 shows an end view of the molded component 46 of FIG. 4. The downstream channel 30 is adapted to fluidly connect to a single lumen 56 in a catheter 58, desirably for an enteral feeding device. As may be discerned from the FIG. 4, additional lumens may be present in the catheter 58 and additional voids may be formed in the molded component 46 if desired.

Figure 6:
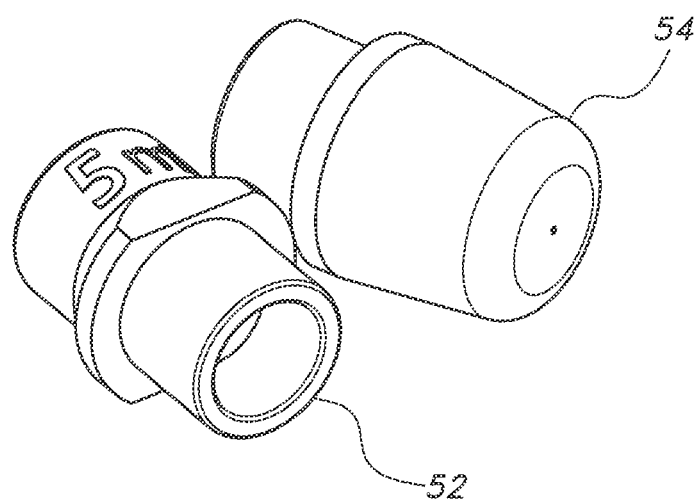
FIG. 6 shows exemplary valves that may be inserted into the voids in the molded component.

FIG. 6 shows exemplary valves 52, 54 that may be inserted into the voids 48, 50 in the molded component 46. The valves may be used, for example, to deliver a gas for fluid through the channel 30 to the catheter lumen 56. In use, each valve may deliver a different substance to the lumen 56 or one valve may be used to deliver a substance to the lumen 56 and the other used to measure the pressure in the lumen 56. Other uses for two valves feeding into a common channel and lumen may be discerned by those skilled in the art.

Figure 7:
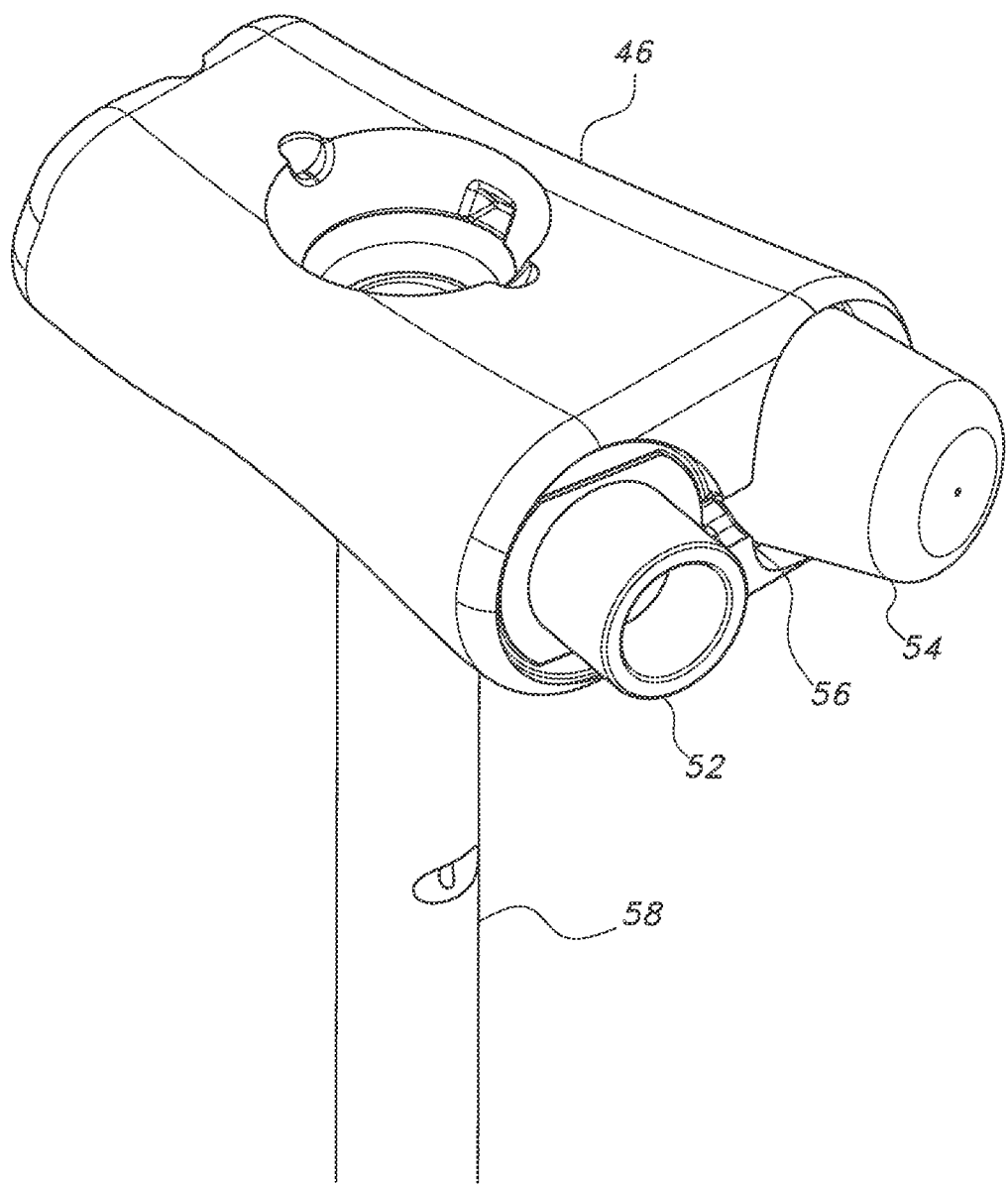
FIG. 7 shows the molded component after insertion of two valves into the voids including a space between the valves.

FIG. 7 shows the molded component 46 after insertion of two valves 52, 54. As should be apparent, there is a small void or space 56 remaining between the valves as an artifact of manufacture. This space 56 allows fluid communication between the channel 30 and the outside atmosphere, which is undesirable.

In order to close or seal the space 56 between the valves 52, 54 and to secure the valves 52, 54 within the molded component 46, an adhesive 60 is used. This adhesive may be one of any number of compatible adhesives curable by temperature, exposure to UV light, etc. Any suitable adhesive may be used provided it solidifies relatively quickly and is compatible with the materials from which the tube is made. By "solidifies relatively quickly" is meant a material that solidifies in a industrially reasonable time, generally less than one hour and more desirably less than 30 minutes and still more desirably less than 5 minutes.

Figure 8:
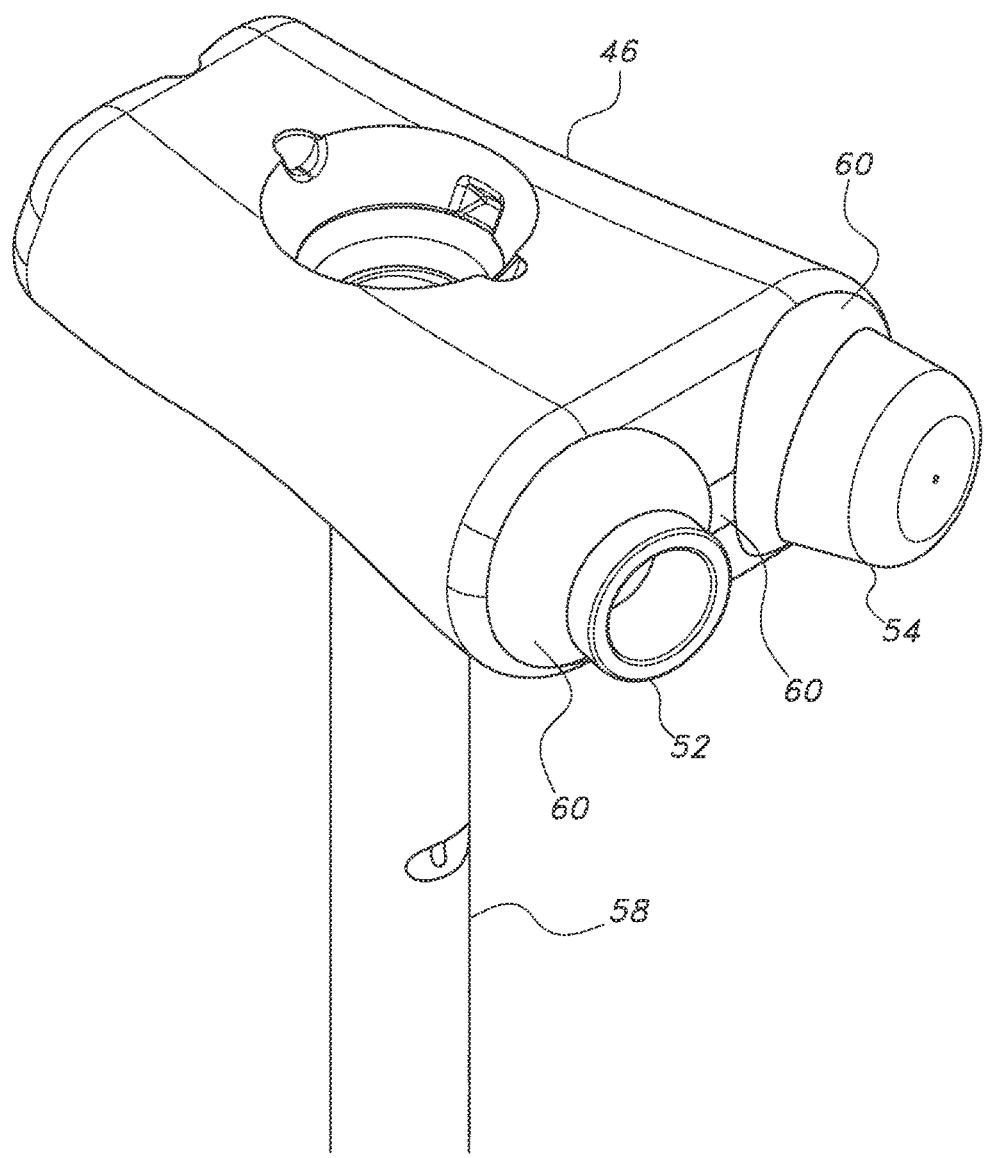
FIG. 8 shows the molded component and valves after the addition of an adhesive to seal the space and secure the valves to the molded component.

FIG. 8 shows the molded component 46 and valves 52, 54 after the addition of an adhesive 60 to seal the space 56 and secure the valves 52, 54 to the molded component 46, and after the adhesive 60 has cured.

While various patents have been incorporated herein by reference, to the extent there is any inconsistency between incorporated material and that of the written specification, the written specification shall control. In addition, while the disclosure has been described in detail with respect to specific embodiments thereof, it will be apparent to those skilled in the art that various alterations, modifications and other changes may be made to the disclosure without departing from the spirit and scope of the present disclosure. It is therefore intended that the claims cover all such modifications, alterations and other changes encompassed by the appended claims.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the invention.

What is claimed is:

1. A single core pin assembly, the assembly comprising a single core pin having a first core pin and at least one second core pin, the first core pin having a first end, a second end and a first core pin body connecting the first end and the second end, the second core pin having a first end, a second end, and a second core pin body connecting the second core pin first end and the second core pin second end, the second core pin first end being configured to join with the first core pin first end to form a common downstream channel.

2. The assembly of claim 1 further comprising a handle used to hold and manipulate the core pin and extract the core pin from a work piece.

3. The assembly of claim 1, wherein the assembly has a higher melting point than a flowable material used with the core pins to form a molded component.

4. The assembly of claim 3, wherein said flowable material surrounds the single core pin assembly in a mold to produce a work piece having the single core pin assembly and a molded component that defines connected voids.

5. A work piece comprising a molded component and the single core pin assembly of claim 1.

6. The molded component of claim 5 wherein said molded component defines connected voids into which valves may be inserted and which connected voids extend into a common downstream channel.

7. The molded component of claim 6 further comprising valves and an adhesive that closes a space between the valves and secures the valves within the molded component.

8. The molded component of claim 6 wherein said common downstream channel is adapted to fluidly connect to a single lumen in a catheter.

* * * * *